US009643157B2

(12) United States Patent
Joshi et al.

(10) Patent No.: US 9,643,157 B2
(45) Date of Patent: May 9, 2017

(54) HYDROGEL COMPOSITION (71) Applicant: New Jersey Institute of Technology, Newark, NJ (US)

(72) Inventors: Bhavita Joshi, Newark, NJ (US); George Collins, Maplewood, NJ (US); Treena Arinzeh, West Orange, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 0 days.

(21) Appl. No.: 15/347,054

(22) Filed: Nov. 9, 2016

(65) Prior Publication Data

US 2017/0050172 A1 Feb. 23, 2017

Related U.S. Application Data (62) Division of application No. 13/552,550, filed on Jul. 18, 2012, now Pat. No. 9,504,987.

(60) Provisional application No. 61/508,998, filed on Jul. 18, 2011.

(51) Int. Cl.
  *B01J 20/26* (2006.01)
  *B01J 20/24* (2006.01)
  *A61L 15/60* (2006.01)
  *B01J 20/28* (2006.01)

(52) U.S. Cl.
  CPC ............ *B01J 20/267* (2013.01); *B01J 20/24* (2013.01); *B01J 20/28047* (2013.01)

(58) Field of Classification Search
  None
  See application file for complete search history.

(56) References Cited

U.S. PATENT DOCUMENTS

| | | | | |
|---|---|---|---|---|
| 4,224,403 A * | 9/1980 | Toda | ......................... | G03C 1/04 430/537 |
| 6,271,278 B1 * | 8/2001 | Park | ......................... | A61L 15/60 521/102 |
| 2010/0038831 A1 * | 2/2010 | Kawaguchi | ............ | B82Y 10/00 264/496 |
| 2010/0198177 A1 * | 8/2010 | Yahiaoui | ................. | A61F 13/82 604/359 |
| 2010/0233234 A1 * | 9/2010 | Arinzeh | ................. | A61K 35/28 424/423 |
| 2011/0287475 A1 * | 11/2011 | Ardekani | ................. | G01N 1/30 435/40.5 |
| 2013/0281378 A1 * | 10/2013 | Muthalagu | ............. | A61K 38/39 514/17.1 |
| 2014/0008569 A1 * | 1/2014 | Joshi | ...................... | B01J 20/265 252/194 |

(Continued)

*Primary Examiner* — Joseph D Anthony
(74) *Attorney, Agent, or Firm* — McCarter & English, LLP (57) ABSTRACT A hydrogel composition is provided that includes crosslinked dextran and dextran sulfate. The hydrogel composition may be included in a matrix that includes an osmotically active material immobilized in the matrix. The hydrogel composition can be combined into superabsorbent preparations that are capable of adsorbing large amounts of water. The superabsorbent preparations have advantages in the use of absorbent materials for physiological fluids, such as diapers, incontinence products, wound dressings and the like, as well as agricultural and environmental applications. In addition, biodegradable superabsorbents of the invention can be prepared.

10 Claims, 5 Drawing Sheets (56) References Cited

U.S. PATENT DOCUMENTS

2014/0100111 A1* 4/2014 Schultz, Sr. ......... C09D 101/16
                                                                      504/140

* cited by examiner

HYDROGEL COMPOSITION

CROSS-REFERENCE TO RELATED APPLICATION

The present application is a divisional application that claims priority benefit to a non-provisional patent application entitled "System and Method for Superabsorbent Material," which was filed on Jul. 18, 2012 and assigned Ser. No. 13/552,550 now U.S. Pat. No. 9,504,987. The entire content of the foregoing non-provisional patent application is incorporated herein by reference.

BACKGROUND OF THE INVENTION

Technical Field

This invention relates to superabsorbent compositions comprising a hydrogel matrix and an osmotically active material immobilized in the matrix.

Background Art

Common hydrogels absorb no more than 100% (1 g water/1 g hydrogel). Superabsorbent materials are hydrophilic polymer networks which can absorb water from 1000-100,000% (10 to 1000 g/g) their dry weight, with typical values on the order of 1000 to 30,000% (10 to 300 g/g). Hydrogels are water insoluble in aqueous environment because of chemical or physical crosslinking between polymer chains. In physically crosslinked hydrogels, polymer network is held together by molecular entanglements or secondary forces including hydrogen bonding or hydrophobic forces. Chemically crosslinked hydrogels are covalently bonded between different polymer chains within the network.

Hydrogels have received a great deal of attention and significant progress has been made in development of these materials for many biological and biomedical applications as well as use as superabsorbents.

Superabsorbent materials are water insoluble and hydrophilic polymer networks which take up water from 10-1000 times of their dry weight. Hydrogels are receiving increasing attention because of their ability to retain great quantity of water and good biocompatibility. Hydrogels may be chemically stable or degrade eventually and dissolve. When a dry hydrogel begins to absorb water, the first water molecules entering the matrix will hydrate the most polar, hydrophilic groups, leading to "primary bound water". As the polar groups are hydrated, the network swells and exposes hydrophobic groups, which also interact with water molecules, leading to "secondary bound water". Primary and secondary bound water are often combined and simply called the "total bound water". After the polar and hydrophobic sites have interacted with and bound water molecules, the network will imbibe additional water, due to the osmotic driving force of the network chains towards infinite dilution. This additional swelling is opposed by the covalent or physical crosslinks, leading to an elastic network retraction force. Thus, the hydrogel will reach an equilibrium swelling level. The additional swelling water that is imbibed after the ionic, polar and hydrophobic groups become saturated with bound water is called "free water" or "bulk water", and is assumed to fill the space between the network chains, and/or the center of larger pores, macropores or voids. As the network swells, if the network chains or crosslinks are degradable, the gel will begin to disintegrate and dissolve, at a rate depending on its composition. However, it has been reported that swelling in aqueous solutions containing salts typically found in physiological fluids cause the swelling to be reduced by as much as 30%. Superabsorbent materials are typically capable of absorbing about 30 g/g in an aqueous solution containing 0.9 weight percent sodium chloride solution in water.

Thus there remains a need for additional hydrogel compositions that absorb a greater percentage of physiological fluids. Additionally there is a need for biodegradable materials for use as superabsorbents, since the current acrylic-based superabsorbents are not biodegradable.

BRIEF DESCRIPTION OF THE INVENTION

It has now been found that compositions of a hydrogel matrix and an osmotically active material immobilized in the matrix can be combined into superabsorbent preparations that are capable of adsorbing large amounts of water.

The absorbent preparations of the invention have advantages in the use of absorbent materials for physiological fluids, such as diapers, incontinence products, wound dressings and the like, as well as agricultural and environmental applications. In addition, biodegradable superabsorbents of the invention can be prepared.

BRIEF DESCRIPTION OF THE DRAWINGS

So that those having ordinary skill in the art will have a better understanding of how to make and use the disclosed gel blends, reference is made to the accompanying figures wherein.

DETAILED DESCRIPTION OF THE INVENTION

It has now been found that a hydrogel matrix and an osmotically active material immobilized in the matrix can be combined into preparations that are capable of adsorbing large amounts of water, based on the weight of the matrix.

The hydrogel matrix of the invention is a water soluble, crosslinkable material such as dextran, starch, polyacrylamide or gelatin. Any source of gelatin is contemplated within the present embodiment including but not limited to porcine, porcine skin type A, bone, bovine hide, and bovine skin. Additionally, the hydrogel matrix of the invention is a crosslinked partially sulfated material such as partially sulfated sodium cellulose sulfate, partially sulfated dextran sulfate, partially sulfated chitosan and partially sulfated starch.

The osmotically active material of the invention is an oligomeric or polyionic material that can be immobilized in the hydrogel matrix. Non-limiting examples include chitosan, diethylaminoethyl dextran as well as polyanionic materials such as sulfated polysaccharides, for example, sodium cellulose sulfate, dextran sulfate, sulfated chitosan and sulfated starch. Additional compounds include naturally occurring ionic polysaccharides, such as glycosaminoglycans, including, for example, chondroitin-4-sulfate, chondroitin-6-sulfate, heparin, hyaluronate, dermatan sulfate and keratin sulfate.

A preferred sulfated polysaccharide of the invention is sodium cellulose sulfate (NaCS).

An example of NaCS with three sulfate groups per glucose unit is shown as Compound (I)

(I)

The osmotically active material is mixed in an aqueous solution of the crosslinkable hydrophilic material and the resulting mixture is allowed to gel. In some embodiments of the invention, a crosslinker is added after the dissolution of the components but before the gelling. After gelling, samples of the gels can be cut out using a punch so that their properties can be studied.

Water retention capacity of these hydrogels can be used for other applications such as absorbent materials available in market.

In one embodiment, the hydrogel preparation of the invention can be formed with sulfated polysaccharide immobilized in a gelatin matrix. In a particular embodiment of the present invention, NaCS is immobilized in gelatin to form a biodegradable superabsorbent.

A further embodiment involves blending a fully sulfated polysaccharide with a neutral polysaccharide that is then crosslinked. In this embodiment the sulfated polysaccharide is immobilized in a neutral polysaccharide matrix.

In yet another embodiment of the invention, dextran sulfate in immobilized in a crosslinked dextran matrix.

Chemical crosslinkers that are useful in this invention include those known in the art to be useful such as isosorbide based epoxy crosslinker, genipin, 1-ethyl-3-(3-dimethylaminopropyl) carbodiimide (EDC), and glutaraldehyde.

One of the more widely available bisepoxy crosslinkers is the diether of epichlorohydrin and biphenyl A which forms biphenyl A diglycidylether. This compound is sparingly soluble in water. It is also reported to be possibly carcinogenic and endocrine disruptor and therefore not ideal for the present invention. Surprisingly however, we have found the epichlorohydrin diethers of isosorbide, diisosorbide bisepoxide (Compound II) and monoisosorbide bisepoxide (Compound III) are fully water soluble with no reported toxicity issues.

(II)

(III)

The water solubility makes it well suited for the preparation of hydrogels and is preferentially used in multiple embodiments of the present invention.

In an embodiment of the invention, NaCS can be combined into gel blends that are capable of adsorbing large amounts of water. Typical compositions of this embodiment contain from about 5% NaCS to about 60% NaCS based on the weight of the bovine gel. The swollen gel blends contain from about 92% to about 98% water when swollen with deionized water and from 90% to about 96% absorbed water when placed in phosphate buffered saline (PBS).

In a further embodiment of the present invention fully sulfated NaCS is blended at various levels, between about 1% to about 60% with a partially sulfated polysaccharide and crosslinked with an isosorbide based bisepoxide.

In a further exemplary embodiment, fully sulfated NaCS is blended with a soluble starch. Starches include, but are not limited to various plant sources such as corn, rice, potato and soy.

Multiple embodiments of the present invention both with and without crosslinking agents were then put into water and allowed to swell. In certain examples of exemplary embodiments of the present invention swelling took place in DI water and/or PBS for a period of about 14 to about 16 hours.

Dimensions of the cylindrical samples were measured before and after swelling to measure volume change.

In one embodiment of the present invention containing bulk hydrogels a slightly basic aqueous solution of the polysaccharide containing the isosorbide crosslinker was raised to about 50° C. to accomplish crosslinking.

Multiple embodiments of the present invention were then heated to remove water. One example of the heating protocol utilized by multiple embodiments of the present invention allowed for about 4 hours of heating at approximately 120° C. The degree of swelling was then determined.

Water absorption of swollen hydrogels was measured using the technique of freeze drying. Samples were kept in DI water/PBS to allow swelling for 14-16 hours. Swollen samples were freeze dried over night at 80° C. The weight loss of the samples during freeze drying was measured from which amount of water absorbed by hydrogels was calculated.

Embodiments of a gelatin hydrogel compositions containing different concentrations of NaCS were prepared and change in volume was analyzed by immersing the gels in water and PBS.

The change in diameter of initially gelled gel specimen before and after swelling for certain examples of multiple embodiments of the present invention was determined. Before and after swelling, diameter and height were measured using vernier caliper scale and volume was calculated.

Bulk hydrogels of the invention were studied by characterizing hydrogels from gelatin/NaCS blends. The swollen gel blends contain from about 92% to about 98% water when swollen with deionized water and from 90% to about 96% absorbed water when placed in phosphate buffered saline (PBS). Hydrogels were immersed both in deionized (DI) water and phosphate buffered saline (PBS). Water absorption and volume change were observed. Normalized water absorption by all the hydrogels is observed to be around 90% though the difference in volume change is not same in them. Hydrogels made in water and swollen in water showed highest volume change compared to the hydrogels swollen in PBS. Hydrogels made with crosslinker in it did not show large volume change both in water or PBS.

For certain embodiments of the present invention the percentage volume change in gels when swelled in water observed for the embodiments ranged from 300% to 3000%. The volume change of exemplary embodiments of the present invention when swelled in PBS was also determined to range from 90% to 170%. Comparing the gel swelling while immersing in water and PBS, it was observed that for said embodiments gels swelled approx. 300 times more in water compare to PBS.

Exemplary embodiments were also analyzed and measured utilizing a freeze drying technique. The embodiments were weighed before and after freeze drying. From initial and final weight of the samples, the amount of water removed was calculated. The amount of water absorbed in different embodiments of the present invention was around 90-95% when immersed in water. In case of embodiments utilizing PBS immersion, the water absorption was around 90-95%.

Embodiments of the present invention utilizing deionized water and PBS had similar water absorption of 95% while immersing them in deionized water. Embodiments of the present invention prepared with a crosslinker decreased the absorption to 85%. Similar observations were determined for embodiments immersed in PBS.

Surface morphology of freeze dried hydrogel embodiments were done by SEM. All embodiments of the present invention showed similar morphology. As shown below, embodiments of the present invention do show difference in volume change between embodiments.

Embodiments of the present invention made in water and swollen in water showed highest volume change compared to embodiments of the present invention swollen in PBS.

From the result of FTIR it is clear that carboxyl group peak is not visible in gel. It can be assumed that carboxyl (C≡O) group of gelatin reacts with the epoxy group of the crosslinker.

In these two embodiments described above, the Gibbs-Donnan equilibrium provides the osmotic pressure driving force for the swelling of the polysaccharide hydrogel. The blending embodiment provides the opportunity to choose the materials and optimize the absorption properties.

Fully sulfated polysaccharides cannot be crosslinked because there are no hydroxyl groups available to participate in the crosslinking reaction. A partially sulfated polysaccharide has available hydroxyl groups and provides the opportunity to produce a single component, crosslinked sulfated polysaccharide. Therefore in one embodiment of the present invention, partially sulfated starch is synthesized. In said embodiment, partially sulfated starch is purified and crosslinked using an isosorbide based bisepoxide to form a single component sulfated polysaccharide.

Embodiments of the invention are viable candidates for highly absorbent materials for personal hygiene and waste management.

Although the systems and methods of the present disclosure have been described with reference to exemplary embodiments thereof, the present disclosure is not limited thereby. Indeed, the exemplary embodiments are implementations of the disclosed systems and methods are provided for illustrative and non-limitative purposes. Changes, modifications, enhancements and/or refinements to the disclosed systems and methods may be made without departing from the spirit or scope of the present disclosure. Accordingly, such changes, modifications, enhancements and/or refinements are encompassed within the scope of the present invention.

Material and Methods

Materials

Gelatin from porcine skin type A was purchased from Sigma-Aldrich (St. Louis, Mo.). Sodium cellulose sulfate (NaCS) was generously provided by Dextran Products Ltd., (Scarborough, Ontario, Canada). The molecular weight of sodium cellulose sulfate is $3.04 \times 10^6$ g/mol. The sulfur content of sodium cellulose sulfate as reported by Dextran Products Ltd. is 18.2%. Each glucose unit has at least two sulfate groups.

Partially sulfated polysaccharides were prepared according to known procedures utilizing dry pyridine and chlorosulfonic acid.

Chemical Crosslinker

Diisosorbide bisepoxide and monoisosorbide bisepoxide, the chemical crosslinkers used in this study were synthesized according to known procedures, such as those found in U.S. Pat. Nos. 3,272,845 and 3,041,300

Hydrogel Preparation

Gelatin solutions with various concentrations of NaCS were mixed well by stirring continuously for about 2 hours at 50° C. Solutions of 5%, 10% and 20% of NaCS based on gelatin in water with gelatin (24% w/w water) were used for all experiments. Blends of gelatin/NaCS were allowed to gel at room temperature for 2 hours. For crosslinked hydrogel preparation, crosslinker was added after gelatin/NaCS dissolution and stirred for 10 minutes. Cylindrical samples of gels were cut out using biopsy punch (10 mm inner diameter, Acuderm Inc.; USA,) for further experiments.

Chemical Crosslinking of Hydrogels

Chemical crosslinking was carried out using isosorbide based epoxy crosslinker synthesized in the laboratory. Before adding the crosslinker, gelatin with different concentrations of NaCS solutions were mixed well. Crosslinker was added to the solution at 50° C. while stirring it continuously. Experiments with 20% of crosslinker (based on solid weight of solution) were performed.

Stability Studies/Swelling Volume

Samples of gelatin with different concentrations of NaCS were put in DI water and PBS for 14-16 hours to swell. Gelatin/NaCS solutions having crosslinker in it were heated at 120° C. for 4 hours to allow crosslinking reaction before putting into water. Dimensions of the cylindrical samples were measured before and after swelling to measure volume change.

Swelling Ratio

Gels with different concentrations of NaCS were heated for four hours at 120° C. to remove all water. Dry hydrogel specimens were weighed before and after swelling to measure weight change. Swelling of dry hydrogel films was observed both in DI water and PBS. The degree of swelling was determined according to the following equation:

$$Ds=(Ws-Wo)/Wo\times100$$

Ds=degree of swelling
Wo=weight of gel before swelling
Ws=weight of gel after swelling Freeze Drying Freeze drying also known as lyophilization is a process of drying sample that minimizes damage to its internal structure. Because lyophilization is a relatively complex and expensive form of drying, it is limited to those materials which are sensitive to heat and have delicate structures and substantial value Water absorption of swollen hydrogels was measured using technique of freeze drying. Samples were kept in DI water/PBS to allow swelling for 14-16 hours. Swollen samples were freeze dried over night at 80° C. The weight loss of the samples during freeze drying was measured from which amount of water absorbed by hydrogels was calculated.

Volume Change on Swelling

Figure 1:
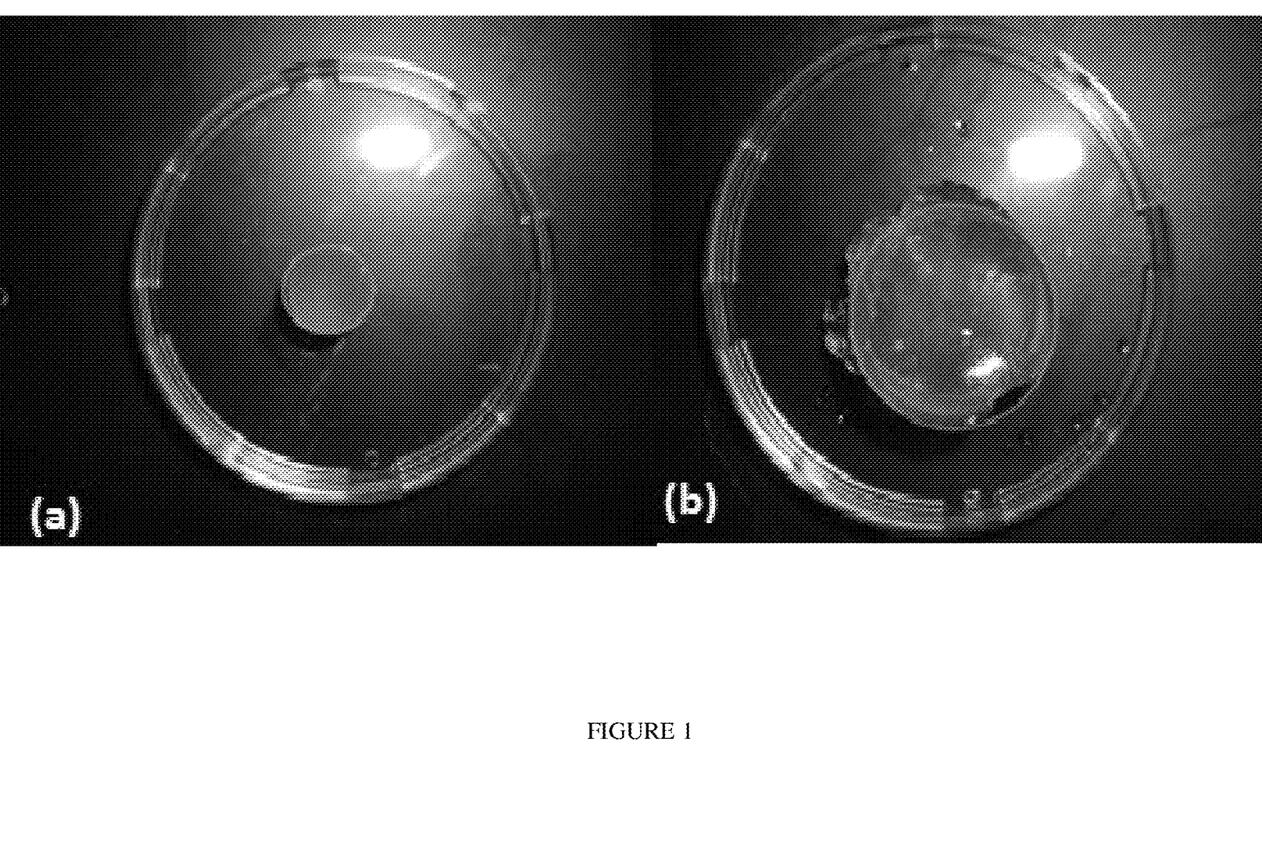
FIG. 1 is a visual representation on one embodiment of the invention before and after fluid uptake.

The gelatin hydrogel constructs containing different concentration of NaCS were prepared and change in volume was analyzed by immersing the gels in water and PBS. FIG. 1 shows the change in diameter of initially gelled gel specimen: (a) before and (b) after swelling. All the swelling values were obtained by immersing cylindrical shaped gel in deionized water and PBS. Before and after swelling, diameter and height were measured using vernier caliper scale and volume was calculated using mathematical formula $$V=\pi r^2 h.$$

Figure 2:
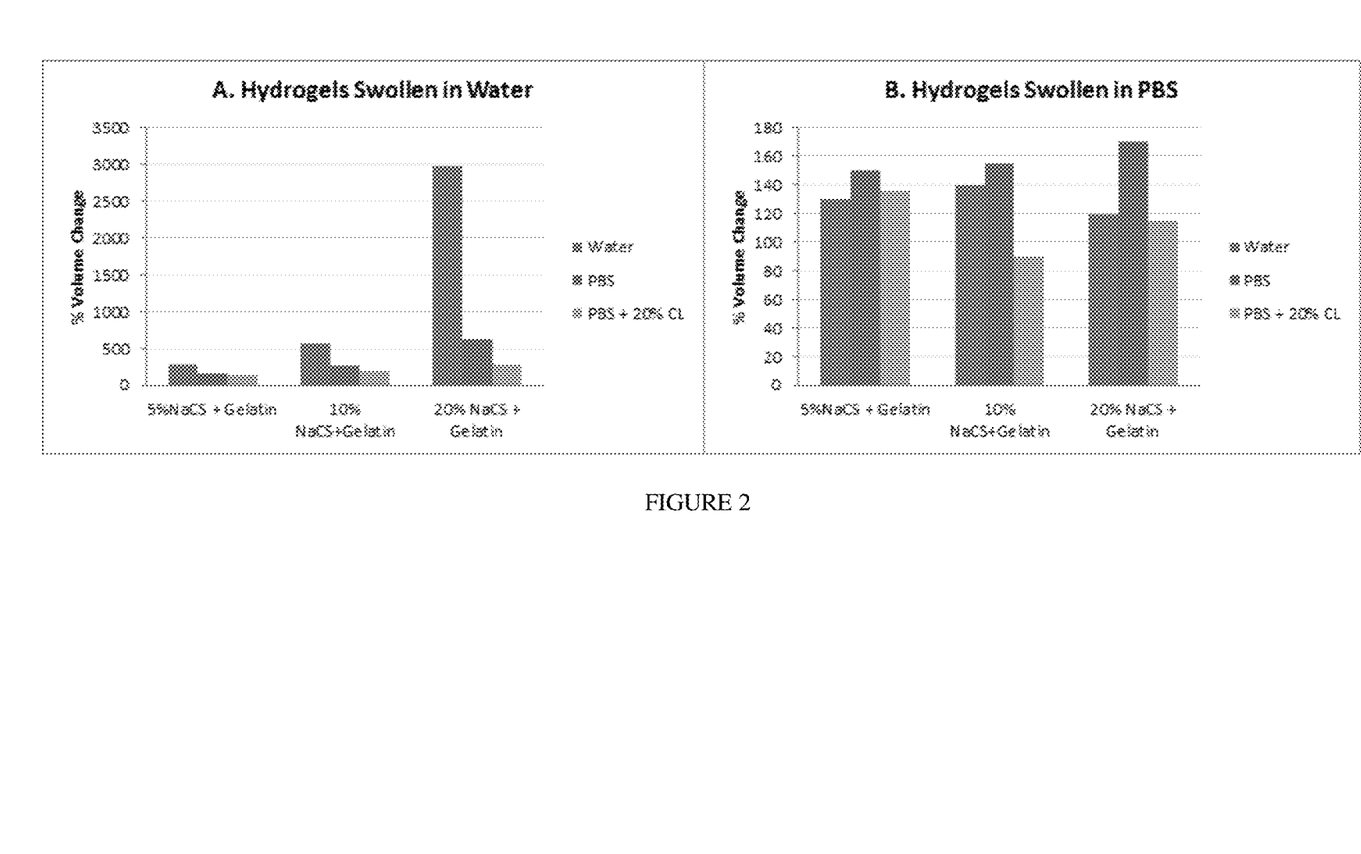
FIG. 2 illustrates volume change in percent of an embodiment of the present invention A) swollen in water; and B) swollen PBS.

FIG. 2 shows the graph of volume change in samples. FIG. 1 (a) shows percentage volume change in gels when swelled in water. Volume change observed here ranges from 300% to 3000%. 20% NaCS solution when made in water shows highest volume change of all other samples. FIG. 2 (b) shows volume change of samples when swelled in PBS. Volume change observed here ranges from 90% to 170%. Comparing the gel swelling while immersing in water and PBS, it was observed that gel swelled approx. 300 times more in water compare to PBS.

Normalized Water Loss

Figure 3:
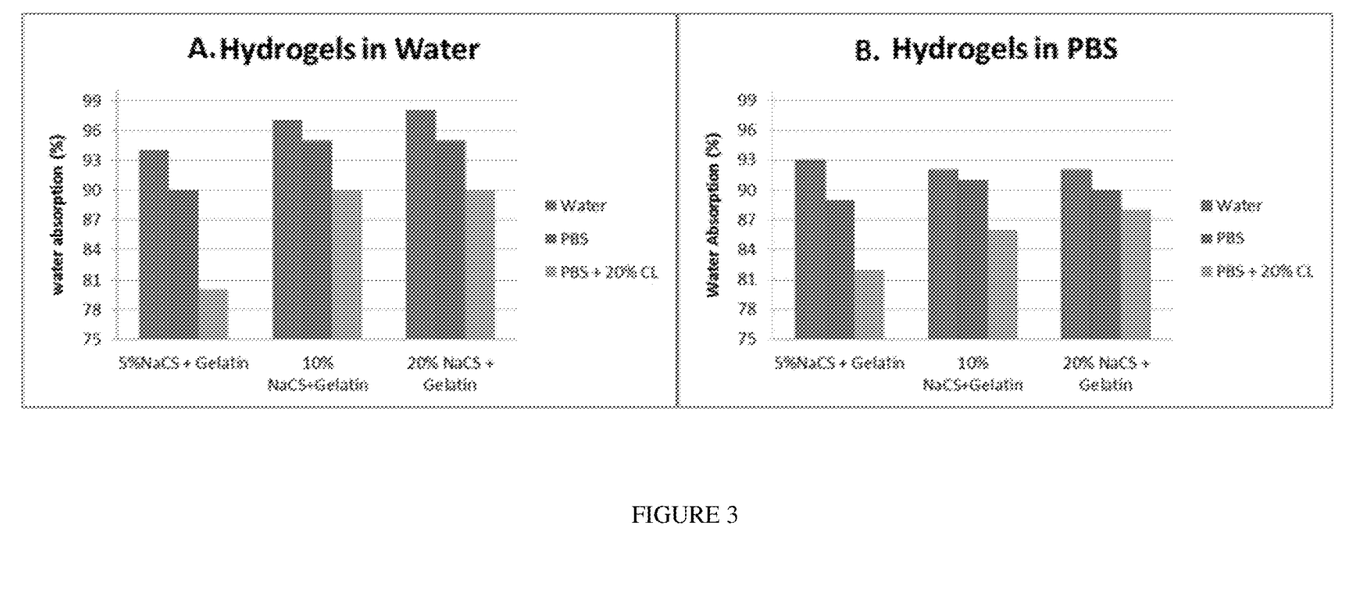
FIG. 3 illustrates water absorption percent of an embodiment of the present invention A) swollen in water; and B) swollen in PBS.

Samples were weighed before and after freeze drying. From initial and final weight of the samples, amount of water removed was calculated. FIG. 3 shows percentage water absorbed by hydrogels. The amount of water absorbed in different hydrogel system was around 90-95% when immersed in water. In case of immersing them in PBS, the water absorption was around 90-95%.

Hydrogels prepared with deionized water and PBS had similar water absorption of 95% while immersing them in deionized water. Water absorption of hydrogels prepared with crosslinker decreased to 85%. Similar observation was determined when hydrogels were immersed in PBS. The hydrogels prepared with crosslinker has absorption of 85% in comparison to that prepared with deionized water and PBS.

Swelling Ratio

Figure 4:
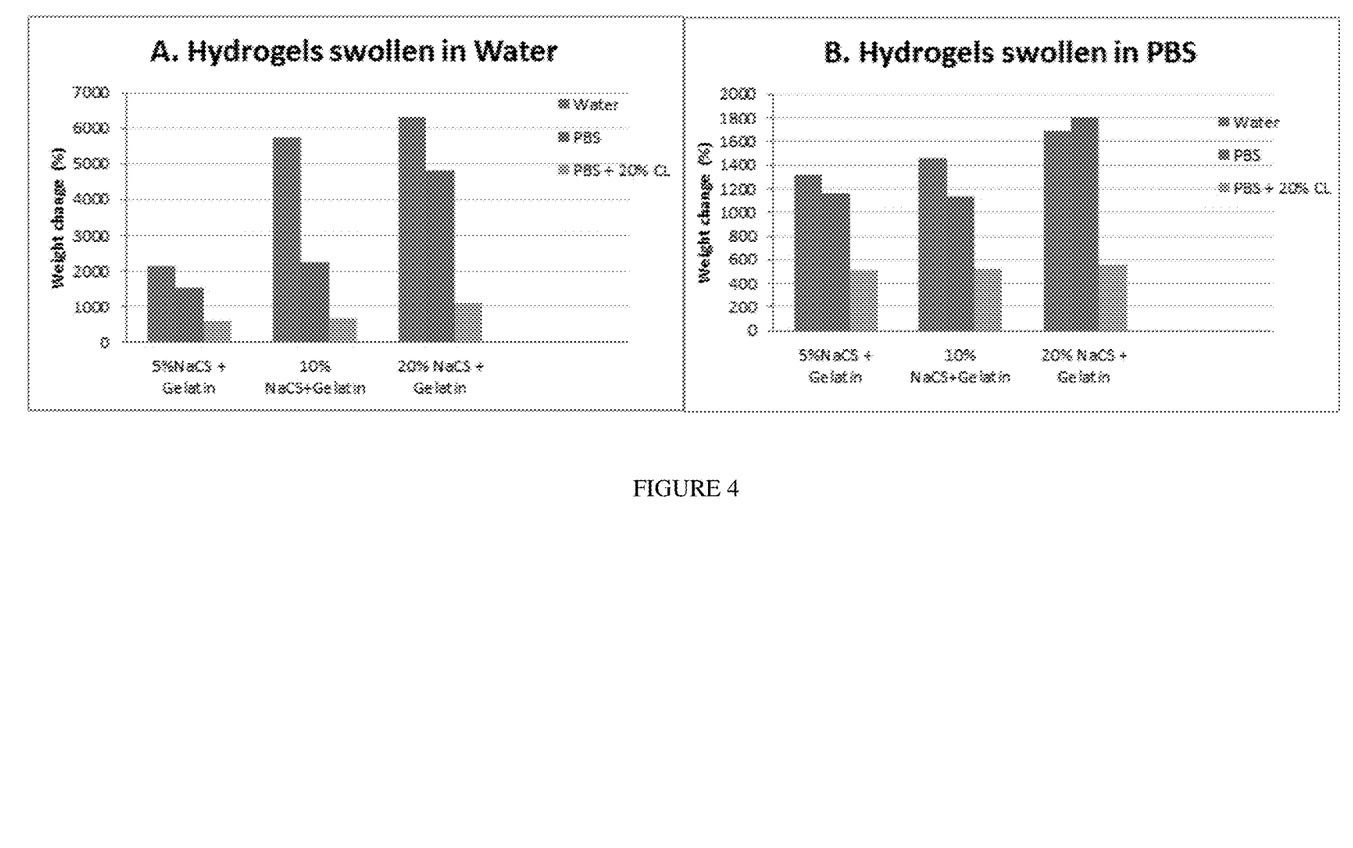
FIG. 4 depicts weight change percent of an embodiment of the present invention A) swollen in water B) swollen in PBS.

The swelling ability of hydrogels was evaluated by measuring the weight gain after rehydration from the dry state in deionized water and PBS for 16 hours. FIG. 4 shows the percentage weight change of these hydrogels after swelling.

Surface Morphology of Superabsorbent

Figure 5:
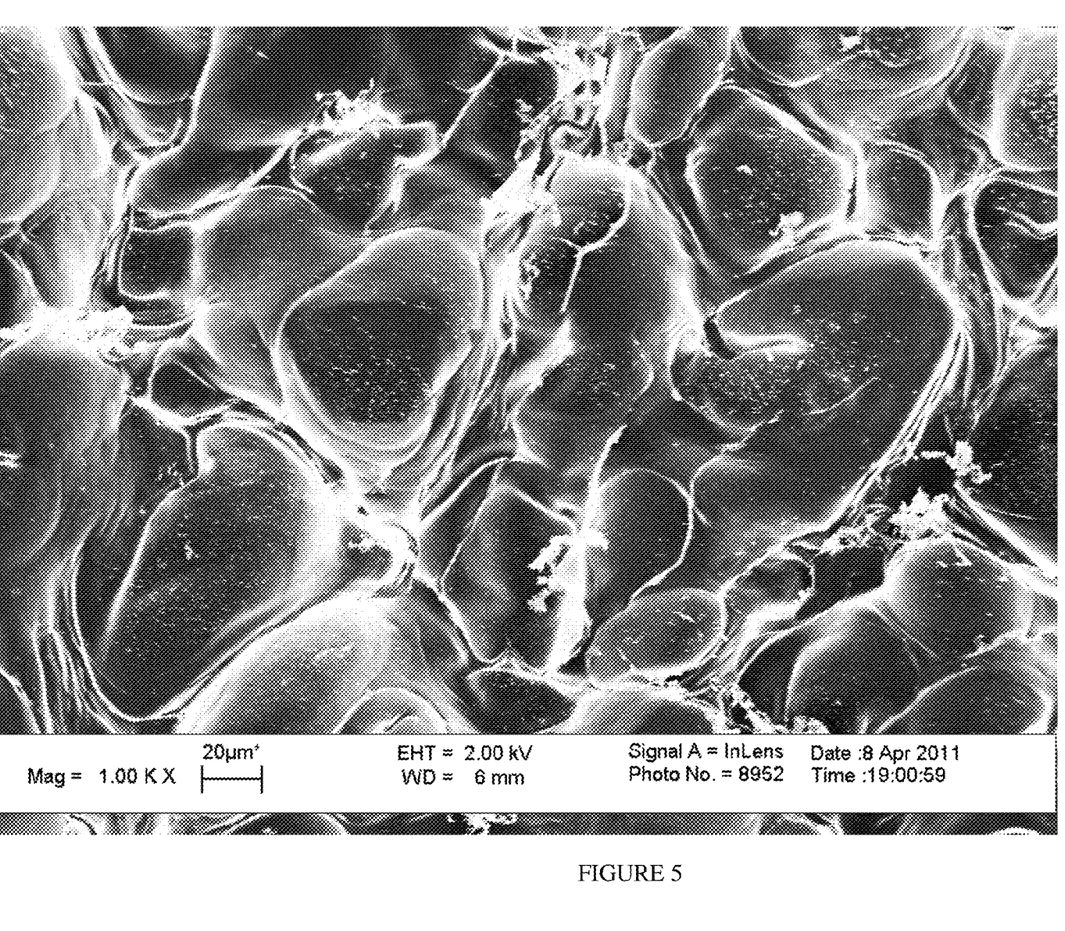
FIG. 5 shows the porous structure of a superabsorbent of the invention via SEM microscopy.

Surface morphology of freeze dried superabsorbents was done by SEM. FIG. 5 shows the porous structure of a superabsorbent of the invention. All the superabsorbents showed similar morphology.

The invention claimed is:

1. A hydrogel composition which comprises crosslinked dextran and dextran sulfate, wherein the dextran sulfate is present in from about 5% to about 60% by weight of the amount of gelatin present in the composition.

2. The composition of claim 1, wherein the dextran sulfate is present in about 5% by weight of the amount of crosslinked dextran present in the composition.

3. The composition of claim 2, wherein the dextran sulfate is present in about 10% by weight of the amount of crosslinked dextran present in the composition.

4. The composition of claim 2, wherein the dextran sulfate is present in about 20% by weight of the amount of crosslinked dextran present in the composition.

5. The composition of claim 1, further comprising an osmotically active material immobilized in a matrix defined by the hydrogel composition.

6. The composition of claim 5, wherein the matrix is a water soluble, crosslinkable material.

7. The composition of claim 5, wherein the osmotically active material is an oligomeric or polyionic material.

8. The composition of claim 5, wherein the osmotically active material is selected from the group of chitosan, diethylaminoethyl dextran, sulfated glycosaminoglycan and sulfated polysaccharide.

9. The composition of claim 5, wherein the osmotically active material is present in from about 5% to about 60% by weight of the amount of the matrix.

10. The composition of claim 9, wherein the osmotically active material is present in about 5% by weight of the amount of the matrix.

* * * * *